United States Patent

Nobuhiko

[11] Patent Number: 5,855,900
[45] Date of Patent: Jan. 5, 1999

[54] SUPRAMOLECULAR-STRUCTURED BIODEGRADABLE POLYMERIC ASSEMBLY FOR DRUG DELIVERY

[76] Inventor: Yui Nobuhiko, Daigakushukusha A-11, 1-1 Ohguchino, Tatsunokuchi-machi, Nomi-gun, Ishikawa-ken, 923-12, Japan

[21] Appl. No.: 637,733
[22] PCT Filed: May 12, 1995
[86] PCT No.: PCT/JP95/00909
§ 371 Date: Apr. 26, 1996
§ 102(e) Date: Apr. 26, 1996
[87] PCT Pub. No.: WO96/09073
PCT Pub. Date: Mar. 28, 1996

[30] Foreign Application Priority Data

Sep. 24, 1994 [JP] Japan .................................. 6/254872

[51] Int. Cl.⁶ .............................. A61F 2/02; A61K 47/30
[52] U.S. Cl. ................................. 424/425; 514/772.3
[58] Field of Search ........................ 424/425; 514/772.3

[56] References Cited

U.S. PATENT DOCUMENTS 5,324,775  6/1994  Rhee et al. ........................ 525/54.5

FOREIGN PATENT DOCUMENTS 60-89418   5/1985  Japan.
60-112713  6/1985  Japan.

Primary Examiner—Carlos Azpuru
Attorney, Agent, or Firm—Spencer & Frank

[57] ABSTRACT

This invention provides as a novel drug carrier into a living body a highly water-soluble polymer that can carry and release a drug at a desired rate and a supramolecular-structured biodegradable polymeric assembly that can release the drug it carries as a function of the specific behavior of biodegradation of a diseased body. A supramolecular-structured biodegradable polymeric assembly according to the invention comprises lots of drug-binding cyclic compounds obtained by combining the drug with α-, β- and γ-cyclodextrins and a linear polymeric chain compound threading through the structural cavity of the cyclic compounds, said linear polymeric chain with biodegradable sites at the both terminals thereof.

8 Claims, 2 Drawing Sheets

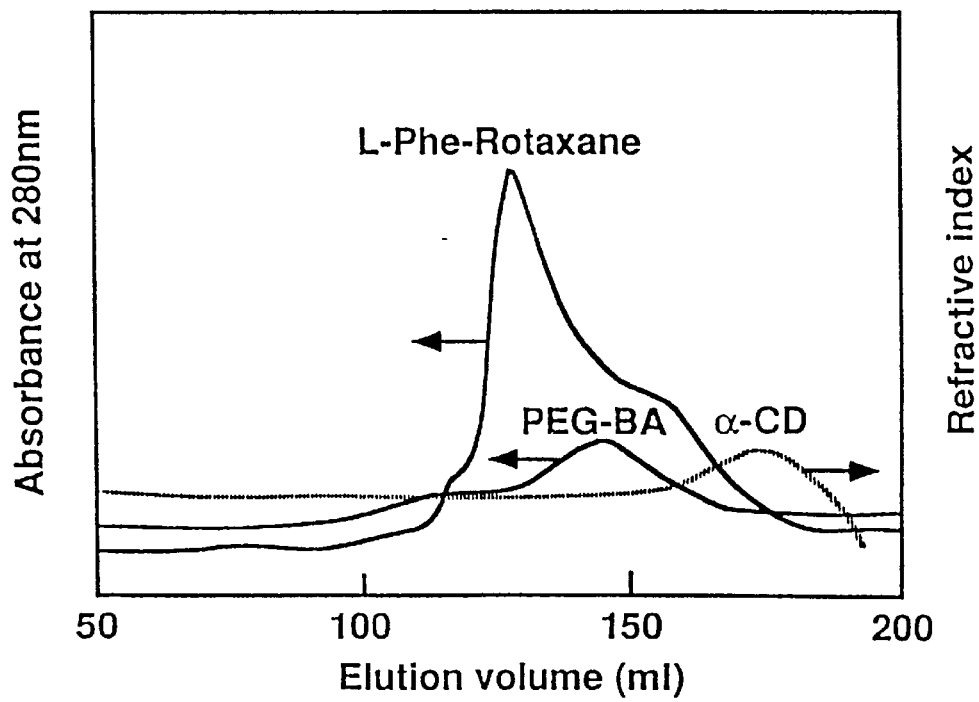
Fig. 1 Gel permeation chromatograms of supramolecular structured biodegradable polymer.
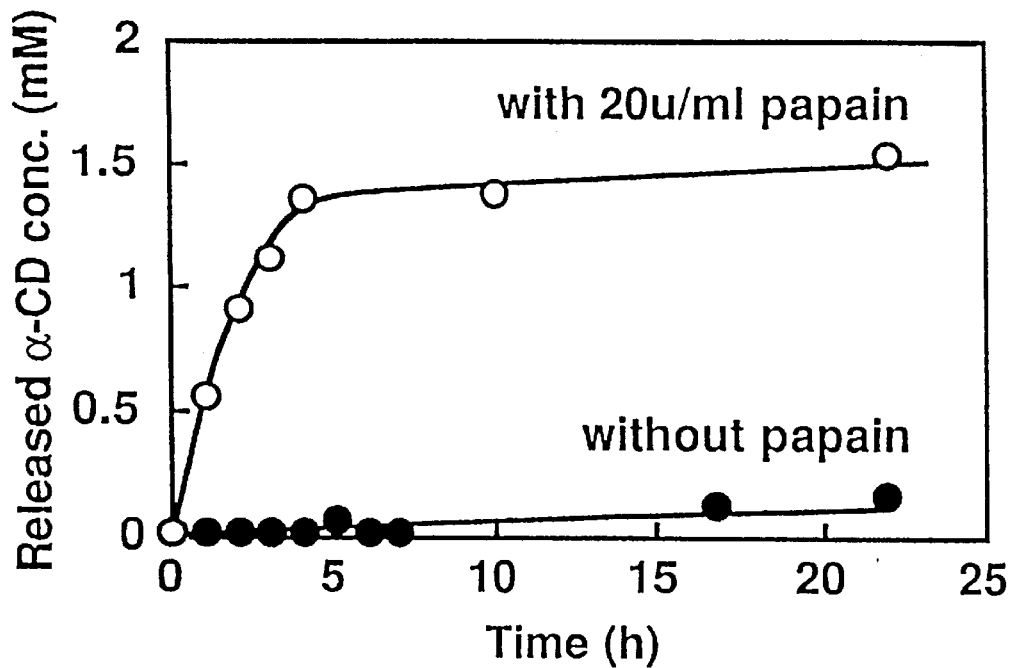
Fig. 2 α-CD release from supramolecular structured bioderadable polymer.

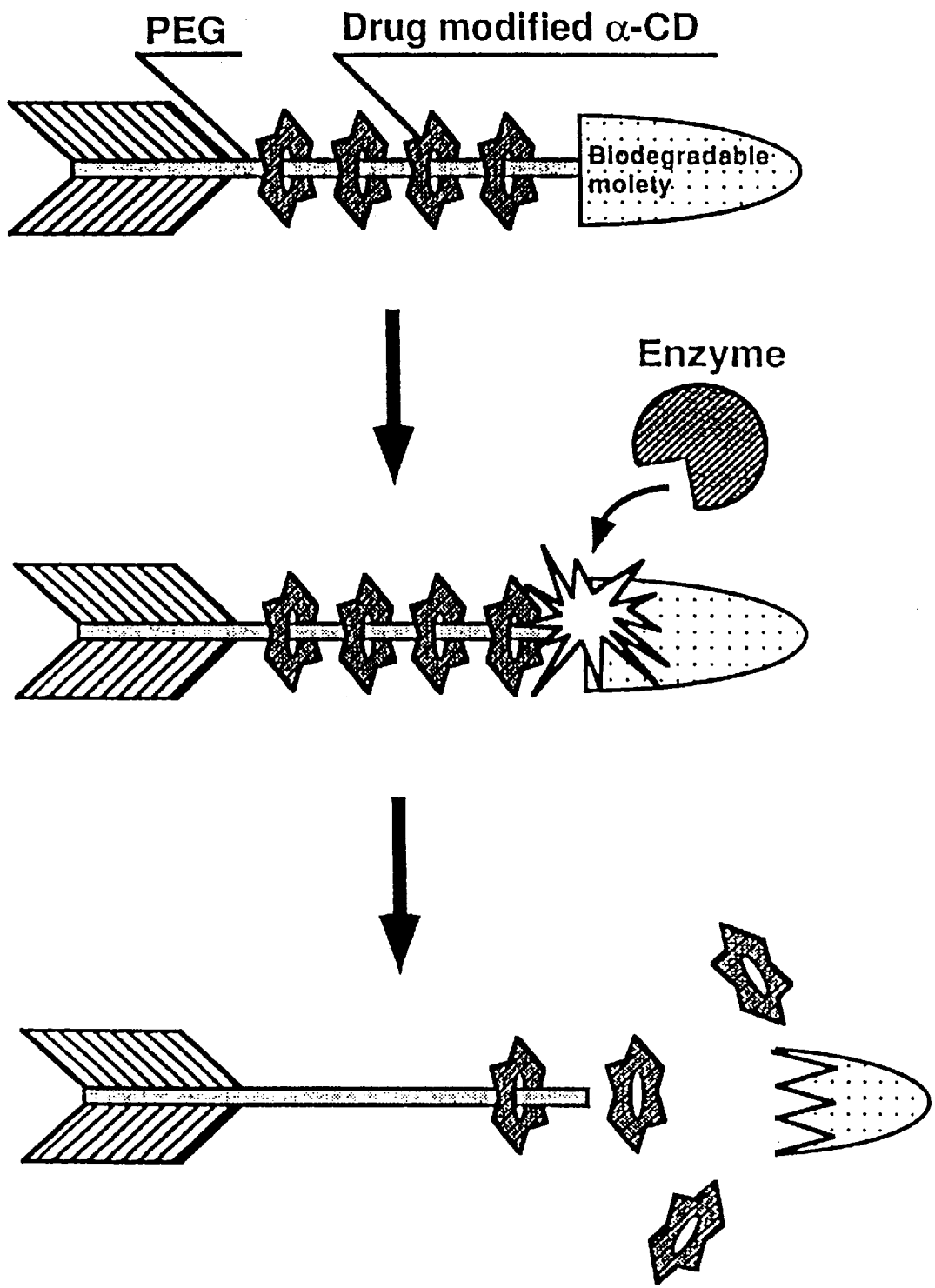
Fig. 3 Drug release by supramolecular structured biodegrdable polymer.

SUPRAMOLECULAR-STRUCTURED BIODEGRADABLE POLYMERIC ASSEMBLY FOR DRUG DELIVERY

BACKGROUND OF THE INVENTION

1. Field of the Invention

This invention relates to a supramolecular-structured biodegradable polymeric assembly with biodegradable moieties at both terminals in the body of the subject.

2. Related Background Art

Of known biodegradable polymers, attention has been paid by researchers on hydrophilic/water soluble polymers designed to effectively deliver drugs linked with covalent and/or ion bonds thereof and hydrophobic polymers that gradually release drugs dissolved or dispersed therein as a result of biodegradation.

While in the former case drug molecules are linked to the polymeric backbones via biodegradable spacer to be in target cells or tissues by enzymatic hydrolysis of the spacers, the chains of such polymers become less soluble or apt to be blocked from accessing hydrolytic enzymes by steric hindrance to consequently reduce their biodegradability if the incorporation of drugs into the polymer is enhanced. The drugs have to be linked with polymeric chains in a manner that is easy both in binding them together and in releasing them from each other by biodegradation and, at the same time, does not damage their activities. In practice, these requirements poses a number of problems to be solved in finding a method of appropriately introducing a drug into polymers.

In the case of polymers of the latter group, they are designed to release the drugs dissolved or dispersed therein by their degradation. In order to achieve degradation-controlled drug release, the drug has to be prevented from undesirable leakage during storage or before the biodegradation of the polymer and, at the same time, the biodegradation of the polymer has to be so control led that the hydrolysis of the polymer takes place only via the surface front.

Normally, biodegradation of a substance occurs via either enzymatic or non-enzymatic hydrolysis. Therefore, from the view point of controlling the rates at both water intrusion and hydrolysis, the substance is inevitably made hydrophobic to reduce the former rate and the biodegradability of the biodegradable groups of the substance is raised to increase the latter rate. These operations for pharmaceutical formulation, however, by turn make the carrier less stable and storable and limit the scope of pharmaceutical applicability and applicable sites of the body.

In short, with known technologies, it is practically impossible to bind a drug to and unbind it from polymer chains in a controlled manner and release the drug into the subject at intended sites at an intended rate. Under these circumstances, there is a strong demand for a novel and highly water soluble polymer that can be used as a carrier for a variety of drugs and is designed to carry a drug and release it at any desired rate and also for a novel hydrophilic gel (hydrogel) that can release the drug it carries in response to a specific biodegradation process observable only in patients.

It is therefore an object of the present invention to provide a supramolecular-structured biodegradable polymeric assembly designed to deliver a drug at an enhanced rate to intended release sites in a highly efficient and reliable way so as to exhibit non-linear (pulse-like) drug release into cells or tissues of the patient.

SUMMARY OF THE INVENTION

According to the invention, unlike any known polymer-drug conjugate or drug-releasing substances, where the drug is linked with polymeric chains or dissolved or dispersed in carrier substances, a drug is carried by a supramolecular assembly.

More specifically, the above object of the invention is achieved by providing a supramolecular-structured biodegradable polymeric assembly comprising lots of drug-modified cyclic compounds obtained by combining a drug with $\alpha$-, $\beta$- and $\gamma$-cyclodextrins and a linear polymeric chain threading through the structural cavity of the cyclic compounds, said linear polymeric chain having biodegradable sites at the both terminals thereof.

Examples of lots of drug-modified cyclic compounds combining a drug with $\alpha$-, $\beta$- and $\gamma$-cyclodextrins include mitonmycin C-cyclodextrin conjugates and conjugates obtained by combining a peptide drug with a relatively small molecular weight and cyclodextrins.

The relationship between the $\alpha$-, $\beta$- and $\gamma$-cyclodextrins to be combined with a drug and the polymer threading through the cyclodextrins has been reported by Dr. Harada (Group "Colloid", Forum "Surface") of Osaka University, who points out that the following polymers can be threaded.
1) $\alpha$-cyclodextrin poly(ethylene glycol)
2) $\beta$-cyclodextrin poly(ethylene glycol), poly(propylene glycol), polyisobutylene
3) $\gamma$-cyclodextrin poly(ethylene glycol), poly(propylene glycol), polyisobutylene, polymethylvinylether Since polymers having bulky groups such as 2,4-dinitrophenyl and 3,6-dinitrobenzoyl groups at the both terminals cannot be threaded, relatively small functional groups such as methyl, methoxy and amine group are preferably used.

The average molecular weight of poly(ethylene glycol), poly (propylene glycol), polyisobutylene or their block-copolymers is between 200 and 5,000 and preferably between 400 and 2,000.

Preferable biodegradable sites of linear polymeric chain polymeric compounds are oligopeptide chains containing from one to five repeating units and comprising as components one or more than one amino acids selected from alanine, valine, leucine, is oleucine, methionine, proline, phenylalanine, tryptophan, aspartic acid, glutamic acid, glycine, serine, threonine, tyrosine, cysteine, lysine, arginine and histidine or oligosaccharide chains containing from one to five repeating units and comprising as components one or more than one of dextran, hyaluronic acid, chitin, chitosan, alginic acid, chondroitin sulfate, starch and pullulan.

A drug to be used for the purpose of the invention is preferably bound to cyclodextrins preferably by a single chain ester or urethane bond that can hardly be subjected to enzymatic degradation because of steric hindrance.

Drugs that can be linked with cyclodextrins for the purpose of the invention include peptide drugs and mitomycin C.

The remarkable feature of a biodegradable polymeric assembly according to the invention is that a drug is not bound to a polymeric chain, and neither dissolved nor dispersed in a polymer compound but held by the formation of a supramolecular polymeric assembly. Therefore, the drug bound to a biodegradable polymeric assembly according to the invention is released not by a process of cleavage of individual polymer-drug linkages but by a process wherein the biodegradation at selected sites to break down the entire assembly in a controlled manner. More specifically, the drug carried by the polymeric assembly is not bound to any polymeric chains so that the entire drug carried by the polymeric assembly may be released into the body of a patient at a selected time as the polymeric assembly is dissociated at all biodegradable sites. The drug may be also released into the body of a patient non-linearly (in a pulse-like manner) by appropriately controlling the rate of dissociating the polymeric assembly at the biodegradable sites, the rate of releasing the drug from the sites it is held to the polymeric assembly and the amount of the drug carried by the polymeric assembly per unit weight of the latter.

A polymeric assembly according to the invention is also advantageous in that it can individually solve the problem of a reduced solubility of the polymeric chain that may arise when a drug is bound thereto, that of selection of the mode of binding a drug to polymeric chains and that of selection of biodegradable sites of the polymeric assembly. A biodegradable polymeric assembly according to the invention can be applied for the preparation of a hydrophilic gel (hydrogel) by crosslinking it at appropriate biodegradable sites located at any of the terminals of the biodegradable polymeric assembly by means of a crosslinking agent in order to prevent the drug held to the polymeric assembly from leaking out unless the latter is dissociated.

BRIEF DESCRIPTION OF THE DRAWINGS

FIG. 1 is a graph schematically illustrating the result of a gel permeation chromatography analysis conducted on a supramolecular-structured biodegradable polymeric assembly according to the invention.

FIG. 2 is a graph showing the lime course of the amount of α-cyclodextrin conjugates released from a supramolecular-structured biodegradable polymeric assembly.

FIG. 3 is a schematic illustration showing how the drug held to a supramolecular-structured biodegradable polymeric assembly is released from the latter.

DESCRIPTION OF THE BEST MODES OF CARRYING OUT THE INVENTION

Now, the present invention will be described by way of examples.

EXAMPLE-1

A supramolecular-structured biodegradable polymeric assembly according to the invention was prepared by way of steps A through D as described below.

A) Preparation of Polyrotaxane

An aqueous solution (10wt%) of poly(ethylene glycol) terminated in amines (PEG-BA, Mn=1200) was added dropwise to a saturated aqueous solution of a drug (mitomycin C) modified α-cyclodextrin and stirred to obtain a white precipitate (polyrotaxane).

B) Introduction of L-Phe to the Both Terminals of the Polyrotaxane

An excessive amount of N-terminal protected L-phenylalanine (Z-L-Phe) (3.38mmol) was dissolved into dimethylformamide (DMF), to which triethylamine (3.72mmol) and hydrochloric acid-ethyl-3-(3-dimethylaminopropyl)carbodiimide (3.72mmol) were added and stirred for 6 hours at 0° C. Thereafter, polyrotaxane/dimethylformamide suspension (0.169mmol) was added to the mixture to cause them to react with each other for 2 days at room temperature.

C) Removal of the Protective Groups (Z-groups) from the Z-L-Phe Polyrotaxane

Thereafter, the mixture of the reaction products was subjected to catalytic reduction in a hydrogen atmosphere in order to remove the Z-groups from the terminals of the composite product by adding the mixture (2mmol) and palladium-carbon (10wt%) to dimethylformamide (DMF). The reduction was terminated when the opacity due to $Ba(OH)_2$ disappeared.

D) Purification of L-Phe-Polyrotaxane

The obtained composite product was purified by gel permeation chromatography (GPC) using Shephadex G-25 with dimetlhylsulfoxide as a solvent.

E-1) Confirmation of the Structure

The structure of the purified product was confirmed by infrared (IR) spectroscopy and nuclear magnetic resonance (NMR) ($^{13}C$ and $^1H$).

E-2) Results and Discussion

By GPC of the purified biodegradable polymeric assembly, the new peak was observed on the high molecular weight side relative to the starting materials of poly(ethylene glycol)-BA and the composite of drug and α-cyclodextrin (hereinafter referred to as α-CD) (FIG. 1).

The preparation of designed supramolecular-structured polymeric assembly (L-Phe-polyrotaxane) was confirmed by the result of the above GPC in combination with those of the infrared spectroscopy (IR) and the analysis of the nuclear magnetic resonance (NMR) ($^{13}C$ and $^1H$).

F-1) Analysis of Biodegradability

The purified L-Phe-polyrotaxane was dissolved into a papain buffer solution (5 mM of citric acid, 58 mM of $Na_2HPO_4$, 2 mM of EDTA and 10 mM of mercaptoethanol, ph7.1) (20wt%) and the solution was stirred at 37° C. (corresponding to the body temperature).

The enzymatic degradation of the terminal peptide groups of polyrotaxane by papain was analyzed by GPC whereas the drug releasing behavior of the α-CD was analyzed by fluorescent spectroscopic measurement of 1-anilino-8-naphthalenesulfonic acid (ANS) (EX=350.0 nm, Em=500.0 nm).

F-2) Results and Discussion

The enzymatic degradation of the terminal peptide groups of the obtained L-Phe-polyrotaxane and the subsequent release of α-CD were examined to find that the peak of L-Phe-polyrotaxane after 10 hours was shifted to lower molecular weight side in the GPC. Concurrently, the concentration of released α-CD was determined by measuring the fluorescent intensity of ANS to find out that it reached a constant level 5 hours after initiating enzymatic degradetion to confirm the successful release of α-CD from the supramolecular-structured polymeric assembly (FIG. 2).

A similar experiment was carried out without papain to observe no ANS fluorescence (FIG. 2). From these results, it is easily assumed that the prepared biodegradable polymeric assembly included α-CDs with its supramolecular-structure and the α-CD threaded through poly(ethylene glycol) (PEG) was released therefrom as the terminal L-Phe groups were degraded by papain (enzyme).

EXAMPLE-2

In the body, the following hydrolyzing enzymes exist in the listed sites of the gastrointestinal tract.
a) mouth α-amylase, lingual lipase
b) stomach
pepsin, gastric amylase, gastric lipase
c) small intestine
1) pancreatic juice
chymotrypsin, trypsin, pancreatic elastase, carboxypeptidase A, carboxypeptidase B, α-amylase, pancreatic lipase, cholesterol esterase, phospholipase A2
2) brush border bound
α- limit dextrinase, maltase, lactase, sucrase, aminooligopeptidase, aminopeptidase, dipeptidase I, dipeptidase III, dipeptidil, aminopeptidase IV
3) mucosal cytoplasm
dipeptidase, aminotripeptidase, proline, dipeptidase
d) colon
β-glucuronidase, β-galactosidase, β-glucosidase, dextranase, urease, azoreductase, cholanoylglycine, hydrase, hydroxy-steroid, hydroxycholanoyl-dihydroxylase, oxidoreductase As a result of looking into preferable biodegradable binding sites that are subject to enzymatic degradation and capable of being bound to poly(ethylene glycol) at terminals, it was found that oligopeptide chains containing one to five (exclusive) repeating units and comprising as components one or more than one amino acids selected from alanine, valine, leucine, isoleucine, methionine, proline, phenylalanine, tryptophan, aspartic acid, glutamic acid, glycine, serine, threonine, tyrosine, cysteine, lysine, arginine and histidine or oligosaccharide chains containing between one to five (exclusive) repeating units and comprising as components one or more than one of dextran, hyaluronic acid, chitin, chitosan, alginic acid, chondroitin sulfate, starch and pullulan provides sites good for the present invention.

As discussed above by referring to tie examples, a supramolecular-structured biodegradable polymeric assembly according to the invention can be prepared by (1) selecting one or more than one types of cyclodextrins (α, β, γ) to be feasibly combined with a drug, (2) selecting a linear polymeric for threading through the cavity of the drug-cyclodextrin conjugate and (3) selecting terminal sites suitable for biodegradation to take place by the enzymatic hydroasis found in the body of the subject and capable of preventing the deug-cyclodextrin conjugate from leaving the linear polymeric chain.

Industrial Applicability

As described above, a supramolecular structured biodegradable polymeric assembly according to the invention can exhibit non-linear (pulse-like) release of drug it carries at the target site(s) by the enzymatic degradation found in the body of the patient so that an drug administration program can be prepared for the patient to such an enhanced level that cannot be achieved by any known technologies.

In other words a chronopharmacological therapy can be made possible by the present invention to control the dose to the patient as a function of not only the condition of the disease of the patient but also the sensitivity of the patient to the drug to be administered that may be subjected to cyclic changes and many other factors.

Thus, the present invention can pave the way for effectively treating various chronic diseases including diabetes, asthma, rheumatoid arthritis and many others for which improved therapeutic methods are expect.

What is claimed is:

1. A supramolecular-structured biodegradable polymeric assembly, comprising:
   a drug-binding cyclic compound obtained by combining a drug with at least one cyclodextrin selected from the group consisting of α-cyclodextrin, β-cyclodextrin, and γ-cyclodextrin via one of ester bonding or urethane bonding, and
   a polymeric material having a linear polymeric chain which passes through the structural cavity of the cyclodextrin, and which has biodegradable sites at both terminals of the linear polymeric chain.

2. The supramolecular-structured biodegradable polymeric assembly according to claim 1, wherein the polymeric material is selected from the group consisting of polyethylene glycol, polypropylene glycol, polyisobutylene, and block copolymers thereof.

3. The supramolecular-structured biodegradable polymeric assembly according to claim 2, wherein the polymeric material has an average molecular weight ranging between 200 and 5,000.

4. The supramolecular-structured biodegradable polymeric assembly according to claim 3, wherein the polymeric material has an average molecular weight ranging between 400 and 2,000.

5. The supramolecular-structured biodegradable polymeric assembly according to claim 1, wherein the biodegradable sites of the linear polymeric chain are oligopeptide chains containing from 1 to 5 repeating units and comprising as components at least one amino acid selected the group comprising alanine, valine, leucine, isoleucine, methionine, proline, phenylalanine, tryptophan, aspartic acid, glutamic acid, glycine, serine, threonine, tyrosine, cysteine, lysine, arginine and histidine.

6. The supramolecular-structured biodegradable polymeric assembly according to claim 1, wherein the biodegradable sites of the linear polymeric chain are oligosaccharide chains containing from 1 to 5 five repeating units and comprising as components at least one substance selected from the group consisting of dextran, hyaluronic acid, chitin, chitosan, alginic acid, chondroitin sulfate, starch and pullulan.

7. The supramolecular-structured biodegradable polymeric assembly according to claim 1, wherein the drug and the cyclodextrin are linked by one of a single chain ester or urethane bond that is difficult to degrade by enzymatic degradation because of steric hindrance.

8. The supramolecular-structured biodegradable polymeric assembly according to claim 1, wherein the drug is a peptide drug.

* * * * *